United States Patent [19]

Greene et al.

[11] 4,334,079

[45] Jun. 8, 1982

[54] SYNTHESIS OF SUBSTITUTED BENZYL ESTERS

[75] Inventors: James M. Greene, Indianapolis; Charles A. Bunnell, Lafayette, both of Ind.

[73] Assignee: Eli Lilly and Company, Indianapolis, Ind.

[21] Appl. No.: 203,736

[22] Filed: Nov. 3, 1980

[51] Int. Cl.³ .............................................. C07C 69/76
[52] U.S. Cl. ..................................... 560/75; 560/55; 560/105
[58] Field of Search ................................ 560/105, 75

[56] References Cited

U.S. PATENT DOCUMENTS 3,035,084  5/1962  Garman et al. ..................... 560/105
3,928,364 12/1975  Seeger et al. ...................... 560/105
3,968,124  7/1976  Mizutani et al. ................... 560/105
4,199,596  4/1980  Fuchs et al. ....................... 560/105

OTHER PUBLICATIONS

Jones, *Aldrichimica Acta*, 9, 35–45 (1976 #3).

*Primary Examiner*—Paul J. Killos
*Attorney, Agent, or Firm*—Joseph A. Jones; Arthur R. Whale

[57] ABSTRACT

A process for preparing certain substituted benzyl esters of phenylacetic acids by esterification in a solvent in which the salt of the acid is insoluble, and in the presence of a phase transfer catalyst.

25 Claims, No Drawings

SYNTHESIS OF SUBSTITUTED BENZYL ESTERS

BACKGROUND

1. Field of the Invention

This invention belongs to the field of synthetic organic chemistry, and provides a method of preparing certain substituted benzyl esters of phenylacetic acids, which process is carried out with the assistance of a phase transfer catalyst.

2. State of the Art

Phase transfer catalysts are used to assist in a number of types of organic reactions, and are usually used to facilitate reaction between one reagent which is dissolved in an aqueous phase, and another reagent dissolved in an organic phase. For example, U.S. Pat. No. 4,072,677, of Beecham Group Limited, shows the synthesis of certain penicillin esters by esterification in systems such as dichloromethane/water, using phase transfer catalysts (ptc) such as tetrabutylammonium bromide, cetyltrimethylammonium bromide and the like.

The use of ptc's has been taught by many commentators in the chemical literature. The compounds used as ptc's, in general, are either quaternary ammonium salts or crown ethers. The following references are typical.

Starks, *Chemtech*, 110–17 (Feb. 1980);
Jones, *Aldrichimica Acta* 9, 35–45 (1976 No. 3);
Hennis et al., *I. and E. C. Prod. Res. and Dev.* 7, 96–101 (1968).

SUMMARY OF THE INVENTION

This invention provides a process for preparing a compound of the formula

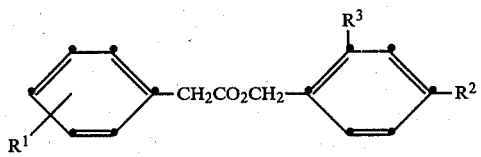

wherein
R$^1$ is hydroxy, protected hydroxy, hydrogen, C$_1$–C$_4$ alkyl, C$_1$–C$_4$ alkoxy or halo;
one of R$^2$ and R$^3$ is hydrogen and the other is phenoxy or C$_1$–C$_6$ alkoxy;
by reacting a compound of the formula

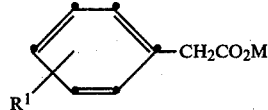

with a compound of the formula

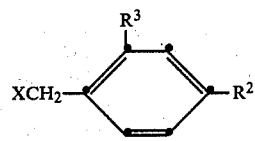

wherein M is sodium or potassium, and X is chloro or bromo; in an organic solvent which is inert to esterification and in which the phenylacetic acid salt is substantially insoluble, and in the presence of a catalytic amount of a phase transfer catalyst of the formula $$X^1NR^4R^5R^6R^7$$

wherein
X$^1$ is chloro, bromo, iodo, toluenesulfonate or methanesulfonate;
R$^4$ and R$^5$ are independently C$_1$–C$_{16}$ alkyl, phenyl or benzyl;
R$^6$ and R$^7$ are independently C$_1$–C$_{16}$ alkyl;
provided that, when X$^1$ is a group other than iodo, the process is carried out in the presence of from about 0.1 to about 0.5 mole of an alkali metal iodide per mole of product to be produced.

DESCRIPTION OF THE PREFERRED EMBODIMENTS

Temperature will be expressed in this document in degrees Celsius. All expressions of concentration, ratios and the like will refer to measurements by weight, unless otherwise stated.

General chemical terms carry their usual meanings in this document. For example, the terms C$_1$–C$_4$ alkyl, C$_1$–C$_4$ alkoxy and C$_1$–C$_6$ alkoxy refer to groups such as methyl, ethyl, propyl, isopropyl, butyl, t-butyl, methoxy, isopropoxy, s-butoxy, pentyloxy, neopentyloxy, hexyloxy, 2,3-dimethylbutoxy and the like.

The term halo refers to fluoro, chloro, bromo or iodo.

The term C$_1$–C$_{16}$ alkyl includes the C$_1$–C$_4$ alkyl groups just discussed, and also includes larger straight and branched-chain alkyl groups such as hexadecyl, tetradecyl, dodecyl, octyl, pentyl, 4-butyl-3,5-dimethylheptyl, 3,8,9-trimethyldecyl, 2-ethyl-5-methyl-4-propyloctyl and the like.

The term protected hydroxy refers to a hydroxy group protected with one of the groups recognized in organic chemistry to be readily cleaved and to be useful for such purpose. Such groups include, for example, formyl, acetyl and substituted acetyl such as chloroacetyl, trityl, benzhydryl, 4-nitrobenzyl, acetoacetyl, t-butoxycarbonyl, 4-methoxybenzyloxycarbonyl and the like.

The term alkali metal refers to lithium, sodium and potassium.

Certain classes of the products made by this process are preferred products, and certain conditions of operating the process are preferred conditions. The listing below shows the preferred products and conditions in tabular form. It will be understood that the various preferred conditions and products may be combined to create other, more limited preferred modes of the invention.

(a) R$^1$ is hydroxy or protected hydroxy;
(b) R$^1$ is hydroxy;
(c) R$^1$ is hydrogen;
(d) M is potassium;
(e) One of R$^2$ and R$^3$ is hydrogen and the other is C$_1$–C$_3$ alkoxy;
(f) One of R$^2$ and R$^3$ is hydrogen and the other is methoxy;
(g) R$^2$ is methoxy and R$^3$ is hydrogen;
(h) X is chloro;
(i) The amount of the alkali metal iodide is from about 0.15 mole to about 0.4 mole per mole of product to be produced; f
(j) The alkali metal iodide is a sodium or potassium iodide;

(k) The solvent is an ester, a ketone or a nitrile;
(l) The solvent is a ketone;
(m) The solvent is acetone;
(n) The amount of the ptc is from about 0.001 mole to about 0.1 mole per mole of product to be produced;
(o) The ptc is a tetraalkylammonium chloride or bromide;
(p) The ptc is a tetra($C_1$–$C_8$ alkyl)ammonium chloride or bromide.

The following group of exemplary products of the process of this invention will be mentioned, to assure that the reader fully understands the invention.
4-methoxybenzyl phenylacetate
2-ethoxybenzyl 3-hydroxyphenylacetate
2-propoxybenzyl 3-(2H-tetrahydropyran-2-yloxy)phenylacetate
4-butoxybenzyl 2-formyloxyphenylacetate
4-hexyloxybenzyl 4-acetoxyphenylacetate
4-isopropoxybenzyl 3-chloroacetoxyphenylacetate
4-(s-butoxy)benzyl 4-diphenylmethoxyphenylacetate
4-(2-methylpentyloxy)benzyl 3-trityloxyphenylacetate
4-(3-methylpentyloxy)benzyl 2-methylphenylacetate
4-neopentyloxybenzyl 4-ethylphenylacetate
4-methoxybenzyl 3-isopropylphenylacetate
4-methoxybenzyl 4-(t-butyl)phenylacetate
2-isopropoxybenzyl 3-butylphenylacetate
2-(i-butoxy)benzyl 2-methoxyphenylacetate
2-(1-ethylbutoxy)benzyl 3-propoxyphenylacetate
4-(1-methylpentyloxy)benzyl 4-(s-butoxy)phenylacetate
2-methoxybenzyl 4-chlorophenylacetate
2-methoxybenzyl 3-bromophenylacetate
4-propoxybenzyl 2-iodophenylacetate
2-ethoxybenzyl 4-fluorophenylacetate
4-phenoxybenzyl 4-hydroxyphenylacetate
2-phenoxybenzyl 3-chlorophenylacetate The reader will understand the manner in which reactants are chosen to make any desired product by the process of this invention. For example, the following choices of reactants are typical.

(a) Phenylacetic acid, sodium salt, is reacted with 4-methoxybenzyl bromide to obtain 4-methoxybenzyl phenylacetate;
(b) 3-Butylphenylacetic acid, potassium salt, is reacted with 4-isopropoxybenzyl chloride to obtain 4-isopropoxybenzyl 3-butylphenylacetate;
(c) 4-Chlorophenylacetic acid, sodium salt, is reacted with 2-methoxybenzyl bromide to obtain 2-methoxybenzyl 4-chlorophenylacetate.

The following group of exemplary phase transfer catalysts are mentioned to assure that the reader understands the type of catalysts used in the process of this invention, and can readily choose a suitable catalyst for his own operations.
ethylmethyldiphenylammonium chloride
benzylphenyldipropylammonium bromide
tetrapropylammonium bromide
butyltriethylammonium chloride
hexylmethyldipentylammonium chloride
ethylmethyldioctylammonium bromide
tridecylphenylammonium chloride
benzyldibutyl(3-ethylhexyl)ammonium chloride
decyltri(hexadecyl)ammonium bromide
dihexylmethyl(tetradecyl)ammonium bromide
tri(4-butyldecyl)phenylammonium bromide
tetra(hexadecyl)ammonium chloride
benzyltri(neopentyl)ammonium chloride
dibutylhexadecyl(2-propylhexyl)ammonium bromide
dibenzyldimethylammonium chloride
butylheptylhexadecylmethylammonium chloride
tetraethylammonium iodide
tetrabutylammonium methanesulfonate
tri(decyl)hexadecylammonium iodide
dibutyldiphenylammonium toluenesulfonate
methyltri(tridecyl)ammonium iodide
benzyldioctylphenylammonium iodide
benzyltrihexylammonium toluenesulfonate
benzyldibutyltetradecylammonium toluenesulfonate
dodecyldiethylphenylammonium methanesulfonate
didecyl(hexadecyl)methylammonium methanesulfonate
tri(pentadecyl)pentylammonium iodide The process of this invention is a most unusual application of phase transfer catalysts to an organic chemical reaction, because the reaction uses one dissolved and one solid reactant. Ptc's, of course, are ordinarily used to assist in reactions where the reactants are in different liquid phases, and the ptc assists in transfer across the liquid-liquid interface. As has been stated, the solvent used in this process must be one which does not appreciably dissolve the phenylacetic acid salt which is one of the reactants.

Conventional methods of esterification fail to give economical yields of the product of this process, because the benzyl halide (or the corresponding benzyl alcohol) is unstable under acid conditions. The resonance structure of the compound, created by the combination of the phenyl ring and the alkoxy or phenoxy moiety, is so unstable that, when the compound is exposed to the mineral acid catalyst normally used in esterification, it forms polymeric chains, rather than reacting with the acid to form the desired ester.

While applicants are not bound by any theoretical explanations of their invention, it is believed that the present invention solves the problem, and obtains high yields of the desired ester, by carrying out the reaction at neutral or slightly alkaline conditions, and using the ptc to transfer the organic acid salt into the reaction phase.

The phenylacetic acid reactant is used in the form of its sodium or potassium salt, which salts are of course formed according to the conventional methods, such as simple contact of the acid with a sodium or potassium salt, such as the carbonate, bicarbonate or hydroxide, in an appropriate solvent. As the examples below show, it is quite practical to form the salt in the same reaction mixture used for the process of this invention without a separate salt-formation step.

The benzyl chlorides and bromides which are reacted with the phenylacetic acid salts are common chemicals and are easily prepared by the ordinary methods known to organic chemists.

A small amount of an alkali metal iodide is needed, unless the ptc is an iodide, in which case the alkali metal iodide is optional. As has been stated, from about 0.1 mole to about 0.5 mole (based on the moles of product to be produced) is necessary. The preferred amount of the iodide is from about 0.15 mole to about 0.4 mole per mole of product to be produced.

The requirements of the process limit the choice of solvents rather narrowly, since the solvent must be inert to esterification reactions, must not dissolve the phenylacetic acid salt, and must have reasonable solvency for the benzyl halide. The preferred solvent is acetone. Other effective solvents are chosen from among the ketones, such as methyl ethyl ketone, methyl isobutyl ketone, cyclohexanone, diethyl ketone and the like; the esters, such as ethyl acetate, ethyl formate, ethyl propionate, methyl acetate, methyl butyrate and the like; and the nitriles, including especially acetonitrile and propionitrile. Mixtures of such solvents may be used.

The types of ptc's which are used in the process have been discussed above. Only a very small amount of the ptc is necessary to facilitate the reation; the amount is here referred to as a catalytic amount. Preferred amounts of the ptc are from about 0.001 mole to about 0.1 mole per mole of product to be produced. More preferred amounts of the ptc are in the range from about 0.005 mole to about 0.05 mole per mole of product to be produced.

The process is preferably carried out at moderately elevated temperatures from about 50° to about 100°. It is usually convenient to operate at the reflux temperature of the reaction mixture, which temperature may be adjusted in the usual manner by putting the reaction mixture under pressure or under vacuum to raise or lower the reflux temperature as may be convenient in a given instance. The reflux temperature of the reaction mixture under ambient pressure, when the solvent is acetone, is the most highly preferred temperature. The process may be operated at lower temperatures, such as from about 0° to about 50°, when the speed of the reaction is not a major consideration.

The amount of solvent used in the process is not critical, and need be no more than necessary to dissolve the benzyl halide, the ptc and the expected product. It is unnecessary to use any substantial excess of either the acid salt or the benzyl halide; it has been found that the process goes in excellent yields without any great excess of either of the reactants. It is possible, and may be advisable in a given instance, to use a moderate excess, in the range of from about 1% to about 25%, of the less expensive reactant to assure that the more expensive reactant is fully consumed.

The following examples of processes according to this invention are presented to assure that the reader fully understands how the invention is carried out.

EXAMPLE 1

A 7.6 g, portion of 4-hydroxyphenylacetic acid was added to 100 ml. of acetone, and 7.6 g. of potassium bicarbonate was added. The mixture was stirred under reflux until a heavy white precipitate formed, and then 9.8 g. of freshly prepared 4-methoxybenzyl chloride, 3 g. of potassium iodide and 0.14 g. of tetrabutylammonium chloride were added, and the mixture was stirred under reflux for 18 hours. Much of the acetone evaporated through the condenser, and so 75 ml. of additional acetone was then added. The reaction mixture was cooled and filtered, and the filtrate was evaporated to dryness under vacuum. To the residue was added 75 ml. of ethyl acetate and 75 ml. of water, and the pH of the mixture was adjusted to 7.8 by the addition of sodium bicarbonate. A small amount of sodium thiosulfate was added to remove color, the layers were separated, and the organic layer was evaporated to dryness under vacuum. To the residue was added 30 ml. of toluene and 30 ml. of hexane, and the mixture was stirred and allowed to stand until the off-white product crystallized. It was harvested by filtration and dried under vacuum at 40° to obtain 10.7 g. of 4-methoxybenzyl 4-hydroxyphenylacetate, m.p. 84°-86°, which was identified by nuclear magnetic resonance analysis in DMSOd$_6$, which showed characteristic features at δ9.31 (s, 1H); 7.00 (m, 8H); 5.02 (s, 2H), 3.73 (s, 3H); 3.54 (s, 2H).

EXAMPLE 2

The process of this example was carried out substantially according to Example 1, except that the period of reflux was only 5.5 hours, and, when the layers were separated after the pH adjustment, the water layer was extracted with 50 ml. of ethyl acetate and the extract was added to the organic layer. The product was 12.0 g. of 4-methoxybenzyl 4-hydroxyphenylacetate, identical to the product of Example 1.

EXAMPLE 3

The process of this example was identical to the process of Example 2, except that the amount of potassium iodide was only 1.5 g. The product obtained was 11.5 g. of 4-methoxybenzyl 4-hydroxyphenylacetate, identical to the products of Examples 1 and 2.

EXAMPLE 4

The process of this example was carried out substantially as was the process of Example 2, except that the amount of tetrabutylammonium chloride was only 0.07 g. The product was 11.3 g. of 4-methoxybenzyl 4-hydroxyphenylacetate, identical to the products of the examples above.

EXAMPLE 5

A mixture of 100 ml. of acetone, 8.25 g. of 4-hydroxyphenylacetic acid and 8.25 g. of potassium bicarbonate was stirred under reflux for 1 hour. To it was added 9.8 g. of 4-methoxybenzyl chloride, 3.3 g. of potassium iodide and 0.15 g. of tetrabutylammonium bromide. The mixture was then stirred under reflux for 6 hours, and overnight at ambient temperature. To the mixture was added 75 ml. of water, and the acetone was removed under vacuum at about 30°. A 100 ml. portion of toluene was then added, and the mixture was stirred and warmed to about 45°. A small amount of sodium thiosulfate was added, and the layers were separated. The aqueous layer was extracted with 50 ml. of toluene, and the extract was added to the organic layer. The combined organics were evaporated to a volume of about 60 ml. under vacuum, and 60 ml. of hexane was added after the residue was cooled to 0°. The mixture was filtered, and the solids were washed with cold hexane and dried under vacuum at 40° to obtain 13.2 g. of 4-methoxybenzyl 4-hydroxyphenylacetate, identical to the products of the examples above.

EXAMPLE 6

The process of this example was carried out according to the process of Example 5, except that the preliminary separate step of forming the salt of the acid was not performed. Instead, the acid, sodium bicarbonate, potassium iodide, benzyl alcohol and tetrabutylammonium bromide were all added at once to the acetone, and the mixture was immediately heated with stirring to reflux. The product of the process was 13.3 g. of 4-methoxybenzyl 4-hydroxyphenylacetate identical to the products of the earlier examples.

EXAMPLE 7

To 100 ml. of acetone were added 8.25 g. of 4-hydroxyphenylacetic acid, 8.25 g. of potassium bicarbonate, 3.58 g. of potassium iodide, 9.78 g. of 4-methoxybenzyl chloride, and 0.6 g. of tetramethylammonium chloride. The mixture was heated to reflux, and processed and worked up as described under Example 5. The product was 13.6 g. of 4-methoxybenzyl 4-hydroxyphenylacetate, identical to the products of Examples 1-6.

EXAMPLE 8

To a jacketed still equipped with a reflux condenser and a nitrogen purge were added 600 liters of acetone, 68 kg. of 4-methoxybenzyl chloride, 50 kg. of 4-hydroxyphenylacetic acid, 20 kg. of potassium iodide, 50 kg. of potassium bicarbonate, and 1 kg. of tetrabutylammonium bromide. The mixture was stirred under reflux for 6 hours and was then cooled to ambient temperature. To the mixture was added 700 liters of deionized water, and the acetone was removed under vacuum, holding the temperature below 45°. To the mixture was then added 700 liters of toluene and 1 kg. of sodium thiosulfate. The mixture was warmed to 45°–50° and stirred for 15 minutes. The layers were then separated, and the aqueous layer was extracted with 300 liters of toluene. The toluene extract was added to the still which contained the original organic layer, and the combined contents of the still was washed with 100 liters of deionized water. The washed toluene solution was then distilled under vacuum, holding the temperature below 40°, until the volume was only 350 liters. The residue was cooled to 0°–5°, and to it was added 300 liters of hexane. The mixture was stirred at constant temperature for 1 hour, and was filtered. The solids were washed on the filter with a mixture of 50 liters of hexane and 50 liters of toluene, and the washed product was dried at 40° to obtain 88.2 kg. of crude 4-methoxybenzyl 4-hydroxyphenylacetate, which was found to be 89% pure by high pressure liquid chromatographic analysis, using a sample of authentic compound as the standard. The impure product was slurried in 400 liters of toluene and 100 liters of hexane, filtered and dried to obtain 69 kg. of purified product, which analyzed 98.2% pure.

EXAMPLE 9

To a flask was added 8.25 g. of 4-hydroxyphenylacetic acid, 8.25 g. of potassium bicarbonate, 0.4 g. of tetrabutylammonium iodide and 80 ml. of acetone. The mixture was stirred under reflux for 1 hour, and then 9.8 g. of 4-methoxybenzyl chloride was added with 20 ml. of acetone. The mixture was stirred under reflux for 6 hours and was then stirred overnight at ambient temperature. The reaction mixture was worked up as described in Example 5 above, to obtain 12.0 g. of 4-methoxybenzyl 4-hydroxyphenylacetate, which was found to be 91.9% pure by high pressure liquid chromatographic analysis.

EXAMPLE 10

The process of this example was run according to the process of Example 9 above, except that the ptc was 0.25 g. of hexadecyltrimethylammonium p-toluenesulfonate, and 3.58 g. of potassium iodide was also added to the reaction mixture. Work-up of the reaction mixture according to the process of Example 5 above gave 13.2 g. of 4-methoxybenzyl 4-hydroxyphenylacetate, which analyzed 96.8% pure by high pressure liquid chromatographic analysis.

The benzyl esters prepared by the process of this invention are used, after further processing, as acylating agents. In particular, they are useful as acylating agents for antibiotic compounds, such as the cephalosporins and the related oxa-beta-lactam compounds.

The compounds are most preferably used by, first, protecting the hydroxy group, if the compound has one, and then inserting a carboxy group on the α-carbon of the phenylacetate group. The α-carboxy compound so produced is used to acylate the amino group of a cephalosporin or related compound, and unnecessary protecting groups are removed.

The resulting antibiotic has a 7-amido group of the formula

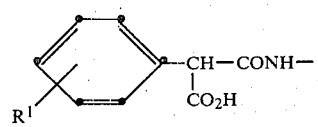

where $R^1$ is as defined above. Such compounds of the cephalosporin series are useful as taught, for example, by U.S. Pat. No. 4,001,226, of Spry. Particularly important products are those where $R^1$ is hydrogen or 4-hydroxy of the oxa-beta-lactam series, as taught by U.S. Pat. Nos. 4,138,486 and 4,201,782, of Narisada.

The use of the products of the process of this invention as acylating agents is illustrated in the Narisada patents, and is typical of the general practice of chemists in carrying out acylations.

More particularly, the hydroxy group of the preferred product of this invention, 4-methoxybenzyl 4-hydroxyphenylacetate, is preferably protected with the 2-tetrahydropyranyl group by reaction with 2,3-dihydropyran. Mild reaction conditions are effective, and the reaction may be carried out in the ordinary inert organic solvents, especially in the halogenated solvents such as dichloromethane, dichloroethane, chloroform and the like. Reaction temperatures from about 0° to about 100° may be used, preferably temperatures from about the ambient temperature to about 50°. It is unnecessary to purify, or even isolate, the protected product.

Insertion of the α-carboxy group is preferably carried out in the presence of a very strong base, of which a preferred base is formed from sodium amide and hexamethyldisilazane. Other bases may be used as well, including the reaction product of an alkyllithium and hexamethyldisilazane, lithium diisopropylamide and the like. The reactions are carried out by bubbling carbon dioxide gas into the reaction mixture at very low temperature, in the range of from about −100° to about 0°, preferably from about −60° to about −30°, in an inert organic solvent, of which ethers are preferred and tetrahydrofuran is particularly preferred.

The carboxylated product is crystallized by the addition of a non-solvent, such as an alkane, and the crystallized α-carboxylated compound is used as an acylating agent in the usual manner. In a particularly preferred acylation, the acylating agent is reacted with a 7β-amino-7α-methoxy-8-oxo-5-oxa-1-azabicyclo-[4.2.0]oct-2-ene-2-carboxylate in a suitable inert organic solvent, and in the presence of a base and a chlorinating agent such as phosphorus oxychloride. The resulting acylated product is an antibiotic compound, in a protected form, which may be de-protected and used as an antibiotic as taught in the literature, for example, in U.S. Pat. No. 4,201,782, of Narisada.

The following preparations illustrate the use of the products of the process of this invention.

PREPARATION 1

4-Methoxybenzyl carboxyl[4-(2H-tetrahydropyran-2-yloxy)phenyl]acetate

An 8.17 g. portion of 4-methoxybenzyl 4-hydroxyphenylacetate was stirred at 40° with 5.05 g. of 2,3-dihydropyran and 0.5 g. of p-toluenesulfonic acid, pyridinium salt, in 50 ml. of toluene for 2 hours. The mixture was filtered, and the filtrate was added to a mixture of 2.2 g. of sodium amide and 9.85 ml. of hexamethyldisilazane which had been stirred under reflux for 3.5 hours in 40 ml. of toluene. The combined solution was stirred at ambient temperature for 30 minutes, and was cooled to −50°. Carbon dioxide was bubbled in at a rate slow enough to hold the temperature below −40°. When the reaction was complete, as indicated by thin layer chromatography, the reaction mixture was warmed to −15°, and 50 ml. of ethyl acetate and 50 ml. of water were added. The temperature of the mixture was held at 0°–5°, and the pH was adjusted to 2.5 with dilute hydrochloric acid. The layers were separated, the water layer was extracted with 50 ml. of ethyl acetate, and the combined organics were evaporated under vacuum to a slurry. To it was added 20 ml. of toluene and 60 ml. of hexane, and the mixture was stirred for 1 hour at 0° and filtered. The solids were dried, and identified as 9.12 g. of the desired product.

PREPARATION 2

Diphenylmethyl 7β-(4-hydroxyphenyl) (4-methoxybenzyloxycarbonyl)acetamido-7α-methoxy-8-oxo-3-(1-methyltetrazol-5-ylthiomethyl)-5-oxa-1-azabicyclo[4.2.0]oct-2-ene-2-carboxylate One hundred ml. of acetone was dried over molecular sieves, and to it was added 10 g. of pulverized diphenylmethyl 7β-amino-7α-methoxy-8-oxo-3-(1-methyltetrazol-5-ylthiomethyl)-5-oxa-1-azabicyclo[4.2.0]oct-2-ene-2-carboxylate and 8.25 g. of 4-methoxybenzyl carboxy[4-(2H-tetrahydropyran-2-yloxy)phenyl]acetate and the mixture was cooled to −10°. To it was added 9.48 ml. of pyridine. The mixture was cooled to −10° again, and 2.7 ml. of phosphorus oxychloride was added very rapidly. The temperature rose to 8°, and after 30 minutes had fallen to 2°. A 4.3 ml. portion of concentrated hydrochloric acid was then added, resulting in an exotherm to 18°. After one hour of stirring, the temperature was down to 12°, and 10.2 ml. of water was added. The mixture was stirred for 5 minutes more, and the layers were separated. The organic layer was seeded with authentic product, and was stirred for about 1.5 hours at 7°–13°. To it was then added 100 ml. of 5% sodium bicarbonate solution over a period of 3 hours at ambient temperature. The mixture was then cooled to 20° in a period of 30 minutes, with stirring, and was filtered. The solids were washed with two 30 ml. portions of water, and were then slurried in 70 ml. of ethyl acetate and 19 ml. of water. The pH of the slurry was lowered to 1.0 with dilute hydrochloric acid, and the layers were separated. The organic layer was stirred in an ice bath for 1 hour, and was then filtered. The solids were washed with 32 ml. of ethyl acetate and vacuum dried at 46° for 4 hours to obtain 12.86 g. of the desired product, which was identified by nuclear magnetic resonance analysis in DMSOd6, which showed characteristic features at δ9.40 (d, 2H); 7.33 (s, 14H); 6.83 (t, 5H); 5.1 (s, 1H); 5.07 (s, 2H); 4.90 (s, 1H); 4.60 (s, 2H); 4.25 (s, 2H); 3.86 (s, 3H); 3.73 (s, 3H); 3.25 (s, 3H).

I claim:

1. A process for preparing a compound of the formula

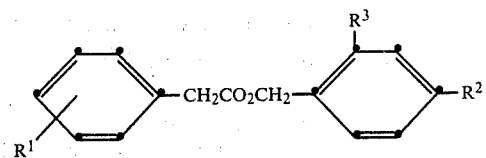

wherein
$R^1$ is hydroxy, protected hydroxy, hydrogen, $C_1$–$C_4$ alkyl, $C_1$–$C_4$ alkoxy or halo;
one of $R^2$ and $R^3$ is hydrogen and the other is phenoxy or $C_1$–$C_6$ alkoxy;
by reacting a compound of the formula

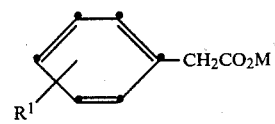

with a compound of the formula

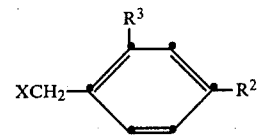

wherein M is sodium or potassium, and X is chloro or bromo; in an organic solvent which is inert to esterification and in which the phenylacetic acid salt is substantially insoluble, and in the presence of a catalytic amount of a phase transfer catalyst of the formula $X^1 NR^4R^5R^6R^7$ wherein
$X^1$ is chloro, bromo, iodo, toluenesulfonate or methanesulfonate;
$R^4$ and $R^5$ are independently $C_1$–$C_{16}$ alkyl, phenyl or benzyl;
$R^6$ and $R^7$ are independently $C_1$–$C_{16}$ alkyl;
provided that, when $X^1$ is a group other than iodo, the process is carried out in the presence of from about 0.1 to about 0.5 mole of an alkali metal iodide per mole of product to be produced.

2. A process of claim 1 wherein the benzyl halide is a compound wherein one of $R^2$ and $R^3$ is hydrogen and the other is methoxy.

3. A process of claim 2 wherein the benzyl halide is a compound wherein $R^2$ is methoxy.

4. A process of claim 1 wherein the phenylacetic acid salt is a compound wherein $R^1$ is hydroxy.

5. A process of claim 3 wherein the phenylacetic acid salt is a compound wherein $R^1$ is hydroxy.

6. A process of claim 5 wherein the phenylacetic acid salt is a potassium salt.

7. A process of claim 6 wherein the benzyl halide is a benzyl chloride.

8. A process of any one of claims 1–7 wherein the phase transfer catalyst is a chloride or bromide, and the alkali metal iodide is a sodium or potassium iodide.

9. A process of any one of claims 1–7 wherein the organic solvent is a ketone.

10. A process of claim 9 wherein the organic solvent is acetone.

11. A process of any one of claims 1–7 wherein the amount of the phase transfer catalyst is from about 0.001 mole to about 0.1 mole per mole of product to be produced.

12. A process of any one of claims 1–7 wherein the phase transfer catalyst is a compound wherein each of $R^4$, $R^5$, $R^6$ and $R^7$ is $C_1$–$C_8$ alkyl.

13. A process of claim 8 wherein the amount of the phase transfer catalyst is from about 0.001 mole to about 0.1 mole per mole of product to be produced.

14. A process of claim 13 wherein the organic solvent is a ketone.

15. A process of claim 14 wherein the organic solvent is acetone.

16. A process of claim 15 wherein the phase transfer catalyst is a compound wherein each of $R^4$, $R^5$, $R^6$ and $R^7$ is $C_1$–$C_8$ alkyl.

17. A process of claim 11 wherein the phase transfer catalyst is an iodide.

18. A process of claim 17 wherein the solvent is a ketone.

19. A process of claim 18 wherein the phase transfer catalyst is a compound wherein each of $R^4$, $R^5$, $R^6$ and $R^7$ is $C_1$–$C_8$ alkyl.

20. A process of claim 11 wherein the phase transfer catalyst is a toluenesulfonate.

21. A process of claim 20 wherein the solvent is a ketone.

22. A process of claim 21 wherein the phase transfer catalyst is a compound wherein each of $R^4$, $R^5$, $R^6$ and $R^7$ is $C_1$–$C_8$ alkyl.

23. A process of claim 11 wherein the phase transfer catalyst is a methanesulfonate.

24. A process of claim 23 wherein the solvent is a ketone.

25. A process of claim 24 wherein the phase transfer catalyst is a compound wherein each of $R^4$, $R^5$, $R^6$ and $R^7$ is $C_1$–$C_8$ alkyl.

* * * * *